United States Patent
Han et al.

(10) Patent No.: US 9,416,089 B2
(45) Date of Patent: Aug. 16, 2016

(54) DIELECTRIC FLUID COMPOSITIONS FOR ENHANCED THERMAL MANAGEMENT

(71) Applicant: DOW GLOBAL TECHNOLOGIES LLC, Midland, MI (US)

(72) Inventors: Suh Joon Han, Belle Mead, NJ (US); Dirk B. Zinkweg, Katy, TX (US); Zenon Lysenko, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/344,937

(22) PCT Filed: Sep. 26, 2012

(86) PCT No.: PCT/US2012/057305
§ 371 (c)(1),
(2) Date: Mar. 14, 2014

(87) PCT Pub. No.: WO2013/049182
PCT Pub. Date: Apr. 4, 2013

(65) Prior Publication Data
US 2014/0346414 A1  Nov. 27, 2014

Related U.S. Application Data

(60) Provisional application No. 61/541,584, filed on Sep. 30, 2011.

(51) Int. Cl.
| | |
|---|---|
| *C09K 5/00* | (2006.01) |
| *C07C 59/01* | (2006.01) |
| *H01B 3/20* | (2006.01) |
| *C07C 51/377* | (2006.01) |
| *H01B 3/24* | (2006.01) |

(52) U.S. Cl.
CPC ............. *C07C 59/01* (2013.01); *C07C 51/377* (2013.01); *H01B 3/20* (2013.01); *H01B 3/24* (2013.01)

(58) Field of Classification Search
None
See application file for complete search history.

(56) References Cited

U.S. PATENT DOCUMENTS

| | | |
|---|---|---|
| 6,340,658 B1 | 1/2002 | Cannon et al. |
| 6,726,857 B2 | 4/2004 | Goedde et al. |

(Continued)

FOREIGN PATENT DOCUMENTS

| | | |
|---|---|---|
| GB | 609133 A | 9/1948 |

OTHER PUBLICATIONS

PCT/US2012/057305, International Search Report & Written Opinion of the International Searching Authority, mailed Feb. 4, 2013.

(Continued)

*Primary Examiner* — Necholus Ogden, Jr.
(74) *Attorney, Agent, or Firm* — Whyte Hirschboeck Dudek S.C.

(57) ABSTRACT

A dielectric fluid composition for electrical apparatus comprises a functionalized 12-hydroxy stearic acid having desirable properties including a pour point less than −30° C. and a fire point greater than 250° C. It may be prepared by a process wherein 12-hydroxy methyl stearate is transesterified by reaction with a C3-C20 alcohol to form an alkyl-12-hydroxy stearate, followed by esterification thereof with a linear or branched C4-C20 carboxylic acid. This acid may be a free acid chloride, a fatty acid, a carboxylic acid anhydride, or combination thereof. The resulting functionalized 12-hydroxy stearic acid exhibits improved thermoxidative capability, low temperature flowability, and increased fire point.

4 Claims, 1 Drawing Sheet

(56) References Cited

U.S. PATENT DOCUMENTS

| | | |
|---|---|---|
| 7,476,344 B2 | 1/2009 | Sunkara et al. |
| 2008/0283803 A1 | 11/2008 | Rapp et al. |
| 2009/0140830 A1 | 6/2009 | Amanullah et al. |

OTHER PUBLICATIONS

PCT/US2012/057305, International Preliminary Report on Patentability, issued Apr. 1, 2014.

Dow Global Technologies LLC, EP Appln. No. 12772638.8, Rejection dated Apr. 9, 2014.

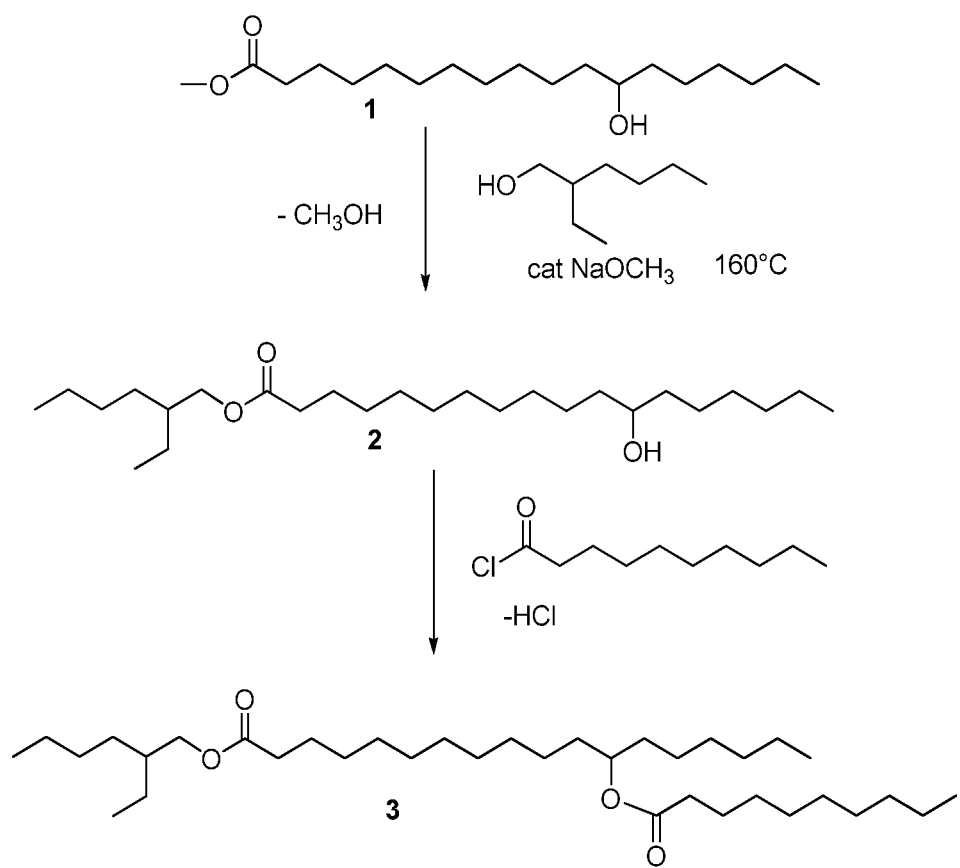

US 9,416,089 B2

DIELECTRIC FLUID COMPOSITIONS FOR ENHANCED THERMAL MANAGEMENT

CROSS-REFERENCE TO RELATED APPLICATIONS

This application is a non-provisional application claiming priority from the U.S. Provisional Patent Application No. 61/541,584, filed on Sep. 30, 2011, entitled "DIELECTRIC FLUID COMPOSITIONS FOR ENHANCED THERMAL MANAGEMENT," the teachings of which are incorporated by reference herein, as if reproduced in full hereinbelow.

BACKGROUND

1. Field of the Invention

The invention relates particularly to the field of dielectric fluids used for thermal management of transformers. More particularly, it relates to improved compositions that provide both electrical insulation and/or heat dissipation for transformers and other apparatus.

2. Background of the Invention

Thermal management of transformers is known to be critical for the safety of transformer operation. Although conventional transformers operate efficiently at relatively high temperatures, excessive heat is detrimental to transformer life. This is because transformers contain electrical insulation which is utilized to prevent energized components or conductors from contacting, or arcing over, the other components, conductors, or internal circuitry. In general, the higher the temperatures experienced by the insulation, the shorter its life. When insulation fails, an internal fault or short circuit, sometimes leading to fire, may occur.

In order to prevent excessive temperature rise and premature transformer failure, transformers are generally filled with a liquid coolant to dissipate the relatively large quantities of heat generated during normal transformer operation. The coolant also functions to electrically insulate the transformer components as a dielectric medium. The dielectric liquid must be able to cool and insulate for the service life of the transfer, which is in a number of applications in excess of twenty years. Because dielectric fluids cool the transformer by convection, the viscosity of a dielectric fluid at various temperatures is one of the key factors in determining its efficiency.

Mineral oils have been tried in various dielectric formulations, particularly because they may offer a degree of thermal and oxidative stability. Unfortunately, however, mineral oils are believed to be environmentally unfriendly and may exhibit unacceptably low fire points, in some cases as low as 150 degrees Celsius (° C.) which is undesirably close to the maximum temperatures to which a dielectric fluid is likely to be exposed during use in a given application, such as a transformer. Because of their low fire points, researchers have sought alternative dielectric materials.

In this search for alternatives, vegetable oils were early-identified as a dielectric medium that could be environmentally friendly and exhibit the desired characteristics of desirably high fire points (significantly greater than 150° C.) and desirable dielectric properties. They may also be biodegradable within a short time. Finally, they may offer enhanced compatibility with solid insulating materials.

Unfortunately, vegetable oil based fluids may suffer from their own drawbacks when compared with mineral oils. For example, vegetable oils may tend to have higher pour points, e.g., greater than 0° C. This is problematic for the many applications where a pour point at or below −15° C. may be required. They may also have an undesirably higher viscosity than a mineral oil based fluid. Thus, researchers seek to identify dielectric fluids that can operate safely and properly within a broad temperature range of from about −15° C. to about 110° C., and which are thermally and oxidatively stable therein.

Researchers looking for alternative have identified a number of possible fluids. For example, U.S. Pat. No. 6,340,658 B1 (Cannon et al.) describes a vegetable oil-based electrically-insulating fluid, which is environmentally friendly and has a high flash point and high fire point. The base oil is hydrogenated to produce maximum possible stability of the oil. Vegetable oils are selected from, e.g., soybean oil and corn oil.

U.S. Patent Publication 2008/0283803 A1 describes a dielectric composition comprising at least one refined, bleached, winterized, deodorized vegetable oil and at least one antioxidant. The dielectric fluid further comprises at least one synthetic ester, wherein the synthetic ester is a bio-based material. The patent defines the term "synthetic ester" as referring to esters produced by a reaction between (1) a bio-based or petroleum derived polyol: and (2) a linear or branched organic acid that may be bio-based or petroleum derived. The term "polyol" refers to alcohols with two or more hydroxyl groups. Suitable examples of the bio-based synthetic esters included are those produced by reacting a polyol with an organic acid with carbon chain lengths of C8-C10 derived from a vegetable oil such as, for example, coconut oil. The synthetic esters also included synthetic pentaerythritol esters with C7-C9 groups. Other polyols suitable for reacting with organic acid to make the synthetic esters include neopentyl glycol, dipentaerythritol, and e-ethylhexyl, n-octyl, isooctyl, isononyl, isodecyl and tridecyl alcohols.

Despite these and other efforts by a variety of researchers, there is still a need to develop dielectric fluids that have the desired combination of properties as well as economic viability and capability for biodegradation.

SUMMARY OF THE INVENTION

In one aspect the invention is a dielectric fluid composition for electrical apparatus comprising a functionalized 12-hydroxy stearic acid having at least one property selected from a number average molecular weight ($M_n$) from 400 Daltons (Da) to 10,000 Da; a dielectric breakdown strength greater than 20 kilovolts/1 mm gap (kV/mm); a dissipation factor less than 0.2 percent (%) at 25° C.; a fire point greater than 250° C.; a kinematic viscosity less than 35 centistokes (cSt) at 40° C.; a pour point less than −30° C.; an acidity less than 0.03 milligrams potassium hydroxide per gram sample (mg KOH/g); and a combination thereof.

In another aspect the invention is a process for preparing a dielectric fluid composition comprising (a) reacting 12-hydroxy methyl stearate and a linear or branched C3 to C20 alcohol under conditions suitable to form an alkyl-12-hydroxy stearate; and (b) reacting the alkyl-12-hydroxy stearate and a carboxylic acid selected from the group consisting of linear and branched C4-C20 free acid chlorides, fatty acids, carboxylic acid anhydrides, and combinations thereof, under conditions suitable to form a functionalized 12-hydroxy stearic acid.

DETAILED DESCRIPTION OF THE EMBODIMENTS

The invention provides a dielectric fluid composition that is useful for thermal management in electrical apparatuses, and has a variety of desirable properties. These properties may include, in specific and non-limiting embodiments, a property, or combination of properties, selected from a dielectric breakdown strength greater than 20 kV/mm gap, a dissipation factor less than 0.2% at 25° C., a fire point greater than 250° C., a kinematic viscosity less than 35 cSt at 40° C., a pour point less than −30° C., and an acidity less than 0.03 mg KOH/g. In addition it may exhibit a number average molecular weight ($M_n$) ranging from 400 Da to 10,000 Da, which helps to ensure a viscosity that is useful in the target applications. The American Society for Testing and Materials (ASTM) standards used to determine these properties are indicated in Table 1 hereinbelow.

TABLE 1

| Property and units | ASTM standard |
| --- | --- |
| Dielectric breakdown strength, kV/mm gap | ASTM D1816 |
| Dissipation factor, % at 25° C. | ASTM D924 |
| Fire point, ° C. | ASTM D92 |
| Kinematic viscosity, cSt at 40° C. | ASTM D445 |
| Pour point, ° C. | ASTM D97 |
| Acidity, mg KOH/g | ASTM D974 |

The dielectric fluid compositions may be prepared starting with either a commercially available product, 12-hydroxy methyl stearate (12-HMS), or, in a pre-process step, from a commonly known and widely available vegetable oil, castor oil. Castor oil comprises primarily ricinoleic acid as its major component (approximately 90 percent of the fatty acid chains), and, in lesser amounts (approximately 10 percent of the fatty acid chains), oleic and linoleic acids, all of which are based on 18-carbon chains. Castor oil itself suffers from relatively poor thermoxidative stability and low temperature flowability.

In order to begin with castor oil as a precursor, the castor oil may typically be hydrogenated and then transesterified by reaction, with, e.g., methanol, to form 12-HMS. This 12-HMS may then be separated from the remaining castor oil products. Since ricinoleic acid includes unsaturation at the ninth ($9^{th}$) carbon of the 18-carbon chain, hydrogenation serves to eliminate this unsaturation. Hydrogenation of castor oil is known in the art and this hydrogenation step may optionally be included simply as a pre-process step with the present invention.

Once the 12-HMS has been procured or prepared, it is ready for use in the first step of the inventive process. This step involves a transesterification of the 12-HMS wherein it is reacted with a linear or branched C3 to C20 alcohol under suitable conditions to form the alkyl-12-hydroxy stearate. In preferred embodiments this alcohol may be a linear or branched C6 to C12 alcohol, and more preferably a linear or branched C8 to C10 alcohol. Preferred conditions for this reaction include a stoichiometric excess of the alcohol, more preferably from three (3) to six (6) times the amount that would be stoichiometric with the 12-HMS, and most preferably four (4) to six (6) times. Also included is use of an effective transesterification catalyst selected from, for example, sodium and potassium bases such as sodium methoxide ($NaOCH_3$); alkyl tin oxides, such as tri-n-butyl tin oxide and dibutyl tin dilaurate; titanate esters; acids such as hydrochloric and sulfuric; and combinations thereof; a temperature ranging from 100° C. to 200° C., more preferably from 120° C. to 190° C., and most preferably from 140° C. to 180° C.; at atmospheric pressure and followed by any suitable distillation such as wiped film evaporation. In this first step reaction the alkyl moiety of the alkyl-12-hydroxy stearate comes from the alcohol residue, i.e., the R in the alcohol formula ROH. Non-limiting examples of C3-C20 alkyl groups would include, in particular embodiments, linear moieties including hexyl, octyl, decyl, and dodecyl, and their corresponding branched moieties, such as ethylhexyl and ethyloctyl.

Once the alkyl-12-hydroxy stearate has been prepared—for example, via a reaction of 12-HMS and 2-ethyl hexanol resulting in a transesterification product that is 2-ethylhexyl-12-hydroxy stearate, or via a reaction of 12-HMS and octanol resulting in a transesterification product that is octyl-12-hydroxy stearate—it is then further esterified, in a second process step, by reacting it with an esterification, or capping, agent. This agent is a linear or branched C4-C20, preferably a C6-C12, and more preferably a C8-C10, carboxylic acid. Such carboxylic acid may be selected from free acid chlorides, fatty acid chlorides, carboxylic acid anhydrides, and combinations thereof. The purpose of this second step is to functionalize the alkyl-12-hydroxy stearate, i.e., to end-cap the free hydroxyl groups, thereby increasing branching to raise the fire point while limiting the viscosity build up.

When this second step is carried out under suitable conditions, the result is a capped oxyalkanoic ester product derived from the 12-hydroxy-alkyl-stearate, i.e., it is a functionalized 12-hydroxy stearic acid. For example, if the first step transesterification product is 2-ethylhexyl-12-hydroxy stearate, and the second step esterification (i.e., capping) is done using a carboxylic acid chloride such as decanoyl chloride, the resulting product is 2-ethylhexyl-12-oxydecanoyl stearate. If the first step transesterification product is 2-ethylhexyl-12-hydroxy stearate, and the second step esterification is done using octanoyl chloride, the result is 2-ethylhexyl-12-oxyoctanoyl stearate. If the first step product is 2-ethylhexyl-12-hydroxy stearate, and the second step esterification is done using isobutyric anhydride, the result is 2-ethylhexyl-12-oxyisobutanoyl stearate. Those skilled in the art will understand that there are many other embodiments of the invention, depending upon the alcohol and capping (esterification) agent selected, and that these examples are provided for illustrative purposes only.

Preferred conditions for this second step reaction include a slight stoichiometric excess of the capping agent (preferably from 1 molar percent (mol %) to 10 mol %, more preferably from 0.5 mol % to 5 mol %, and most preferably from 0.1 mol % to 0.2 mol %). Also included is the use of an effective transesterification catalyst selected from, for example, sodium and potassium bases such as sodium methoxide ($NaOCH_3$); alkyl tin oxides, such as tri-n-butyl tin oxide and dibutyl tin dilaurate; titanate esters; acids such as hydrochloric and sulfuric; and combinations thereof; a temperature ranging from 100° C. to 200° C., more preferably from 120° C. to 190° C., and most preferably from 140° C. to 180° C.; at atmospheric pressure followed by any suitable distillation such as wiped film evaporation. It is noted that at commercial scale, a free carboxylic acid, decanoic acid, may be more more economical than a fatty acid chloride or an anhydride.

The following process schematic is provided as FIG. 1 in order to illustrate the process aspect of the invention. For illustrative purposes only, FIG. 1 shows use of 2-ethyl hexanol as the transesterifying alcohol; $NaOCH_3$ as the catalyst for the transesterification; and a transesterification temperature of 160° C. In the second step of FIG. 1, the esterification of the 2-ethylhexyl-12-hydroxy stearate is accomplished by reaction with decanoyl chloride to form the capped final dielectric fluid, which is 2-ethylhexyl-12-oxydecanoyl stearate.

When prepared as described herein, the novel compositions which may be prepared by the process described hereinabove may exhibit highly desirable properties. For example, they may have an $M_n$ from 400 Da to 10,000 Da, preferably 500 Da to 5,000 Da; a dielectric breakdown greater than 20 kV/mm gap, preferably greater than 25 kV/mm gap; a dissipation factor less than 0.2% at 25° C., preferably less than 0.1% at 25° C.; a fire point greater than 250° C., preferably greater than 300° C.; a kinematic viscosity less than 35 cSt at 40° C., preferably less than 30 cSt at 40° C.; a pour point lower than −30° C., preferably lower than −40° C.; and/or an acidity less than 0.03 mg KOH/g, preferably less than 0.025 mg KOH/g. In some embodiments two or more of these properties may be characteristic of the compositions.

A further advantage to the dielectric fluid compositions of the present invention is that they may be used neat, i.e., at 100 weight percent (wt %) of a dielectric fluid being used in an application such as in a transformer, or they may be combined with, and compatible with, a variety of other dielectric fluids for such applications, at levels ranging from 1 wt % to 100 wt %. In particular embodiments it may be preferred that the inventive compositions comprise from 30 wt % to 90 wt % of such combination fluids, and in more preferred embodiments such may comprise from 40 wt % to 90 wt %, and most preferably from 50 wt % to 90 wt %.

Additional dielectric fluids that may be combined with the dielectric fluid compositions of the present invention may include, in non-limiting example, natural triglycerides such as sunflower oil, canola oil, soy oil, palm oil, rapeseed oil, cottonseed oil, corn oil, coconut oil, and algal oils; genetically modified natural oils such as high oleic sunflower oil and high oleic canola oil; synthetic esters such as pentaerythritol esters; mineral oils such as UniVolt™ electrical insulating oils (available from ExxonMobil); poly alpha olefins such as polyethylene-octene, -hexane, -butylene, -propylene and/or -decalene branched, random co-polyoligomers having $M_n$ values ranging from 500 to 1200 Da; and combinations thereof. It will be obvious to those skilled in the art that inclusion of additional dielectric and/or non-dielectric fluids may significantly alter properties, and that therefore the effect of such should be taken into account according to the targeted application.

Among the advantages of the dielectric fluid compositions of the invention is that they are biodegradable, obtained from renewable resources, and are generally classified as environmentally friendly. Furthermore, because of their relatively high fire points, they are generally less flammable than many of their dielectric competitors. They also show good thermal and hydrolytic stability properties that may serve to extend the insulation system's life.

EXAMPLES

Example 1

12-HMS/2-Ethyl-1-hexanol/Octanoyl Chloride

Day 1: 164.75 grams (g) of 2-ethyl-1-hexanol is weighed into a 1000 milliliter (mL) three neck round bottom flask. A condenser, Dean Stark Trap, thermometer with a thermowatch temperature regulator, an overhead mechanical stirrer, stopper, and $N_2$ inlet are added. The stirrer is turned on. A half-cube of sodium (Na) metal (~0.102 g, flattened, cut into small pieces) is added to the flask. The heat is turned up to 60° C. The Na dissolves after 45 minutes. 100.23 g of 12-HMS is added to the flask. Insulation is wrapped around the flask. The heat is turned up to 160° C. Methanol overhead is collected. The reaction mixes for 6 h and is allowed to continue overnight.

Day 2: After 7 h, GC confirms the reaction is complete and the heat is turned off. 100 mL of toluene is added once the reaction mixture returns to room temperature. The sample is put into a separatory funnel and three (3) 50 mL (each) washes with 1N HCl are done to neutralize the Na. The aqueous layer is discarded. The organic layer is cloudy and put into a 500 mL Erlenmeyer flask. Magnesium sulfate ($MgSO_4$), anhydrous powder, is added to the Erlenmeyer flask until the $MgSO_4$ stops clumping in the flask. The solution is then clear. The $MgSO_4$ is filtered out using a Buchner funnel with a perforated plate attached to an Erlenmeyer. To remove the toluene and excess 2-ethy-1-hexanol, the sample is evaporated using a rotary evaporator ("rotavap") secured with a pump. The water bath is first set at 40° C. to remove the Toluene, and then bumped up to 90° C. to remove the 2-ethyl-1-hexanol. GC confirms there is still an excess of 2-ethyl-1-hexanol, so the sample is put through the WFE using the following conditions.

TABLE 2

Collection conditions for 2-ethylhexyl-12-hydroxy stearate.

| Jacket (° C.) | Cold Finger (° C.) | Stir Speed (rpm) | Pressure (mtorr) | Flow Rate (mL/min) |
|---|---|---|---|---|
| 150 | 10 | 484 | 100 | 2.0 |

100 mtorr = about 0.01 kilopascals (kPa)

Day 3: Addition of octanoyl chloride (1.1 mole excess) is carried out by first weighing 107.00 g of product into a 500 mL three neck round bottom flask. A condenser, thermometer with a thermowatch temperature regulator, an overhead mechanical stirrer, stopper, and $N_2$ inlet are added. The stirrer is turned on. 100 mL of toluene is added. Using an addition funnel, 44.87 g of octanoyl chloride is added. After 1 h, GC confirms that the reaction is complete.

100 mL of methanol is added to the sample. The sample is put on the rotavap to remove the toluene and methanol. GC confirms that some solvent is still present in the sample. The sample is then run down the WFE using the same conditions stated earlier. The overheads are discarded.

The sample is put into a freezer overnight, and in the morning it is discovered that it has not frozen. Acid number is 0.45 mg KOH/g.

Example 2

12-HMS/ME-810* (*a Roughly 50:50 wt % Blend of Octanoic and Decanoic Methyl Esters)

Day 1: 301.41 g of 12-HMS is weighed out into a 1000 mL three-neck, round-bottom flask. A condenser, Dean Stark Trap, thermometer with a thermowatch temperature regulator, an overhead mechanical stirrer and $N_2$ inlet are added. The stirrer is turned on. 410.90 g of ME-810 acid is added. The reaction is heated to 170° C. and the progress of the reaction monitored by GPC until completion. The reaction is passed through the WFE using continuous flow and under following conditions. The bottoms (product) are collected and the overhead is discarded.

TABLE 3

Collection conditions for 12-HMS/ME-810.

| Jacket (° C.) | Cold Finger (° C.) | Stir Speed (rpm) | Pressure (mtorr) | Flow Rate (mL/min) |
|---|---|---|---|---|
| 130 | 20 | 531 | 200 | 6.0 |

200 mtorr = about 0.03 kPa

The product is primarily solids with some liquid and is deemed unacceptable for transformer fluid applications.

Example 3

12-HMS/2-Ethylhexanoic Acid

Day 1: 101.6 g of 12-HMS is weighed into a 500 mL three-neck, round-bottom, flask. A condenser, Dean Stark Trap, thermometer with a thermowatch temperature regulator, an overhead mechanical stirrer, stopper, and $N_2$ inlet are added. 132.9 g of 2-ethylhexanoic acid is added and the stirred reaction is heated to 170° C. After 3 h, the heat is turned off. Progress of the reaction is monitored by GPC. Upon completion, the product is put through the WFE using the following conditions. The overhead is discarded. The solution is a clear, golden yellow color.

TABLE 4

Collection conditions for 2-ethylhexanoic acid.

| Jacket (° C.) | Cold Finger (° C.) | Stir Speed (rpm) | Pressure (mtorr) | Flow Rate (mL/min) |
|---|---|---|---|---|
| 130 | 20 | 397 | 200 | 4.3 |

200 mtorr = about 0.03 kPa

Example 4

12-HMS/2-Ethyl-1-hexanol/Decanoyl Chloride

Day 1: 400.66 g of 2-Ethyl-1-hexanol is weighed into a 2000 mL, three-neck, round bottom flask. A condenser, Dean Stark Trap to collect bi-product, thermometer with a thermowatch temperature regulator, an overhead mechanical stirrer, and $N_2$ inlet are added. Na metal (0.411 g, flattened, cut into small pieces) is added to the stirred reaction and the reaction heated to 60° C. The sodium dissolves after 1 h. 300.54 g of 12-HMS is added to the flask and heated to 160° C. The reaction is mixed overnight. The reaction continues through Day 2 and Day 3.

Day 4: GC confirms the reaction is complete and the reaction is neutralized with 2 mL of 12N HCl at room temperature. The sample is filtered using a 2000 mL Erlenmeyer with a side arm and a 150-g Buchner funnel with filter paper. The sample is a very bright orange color. To remove the excess 2-ethyl-1-hexanol, the sample is evaporated in vacuo. GC confirms there is still an excess of 2-ethyl-1-hexanol, so the sample is put through the WFE using the following conditions.

TABLE 4

Collection conditions for excess 2-ethyl-1-hexanol.

| Jacket (° C.) | Cold Finger (° C.) | Stir Speed (rpm) | Pressure (mtorr) | Flow Rate (mL/min) |
|---|---|---|---|---|
| 140 | 10 | 492 | 100 | 1.5 |

100 mtorr = about 0.01 kPa

GPC analysis reveals the presence of dimeric species and the product is removed via a WFE under the following conditions.

TABLE 5

Collection conditions for 2-ethylhexyl-12-hydroxyl stearate.

| Jacket (° C.) | Cold Finger (° C.) | Stir Speed (rpm) | Pressure (mtorr) | Flow Rate (mL/min) |
|---|---|---|---|---|
| 240 | 20 | 387 | 100 | 1.5 |

100 mtorr = 0.01 kPa

GC analysis reveals that only the desired material is isolated in the distillate or overhead fraction 350.12 g of this product is weighed into a 2000 mL, three-neck, round-bottom flask. A condenser, thermometer with a thermowatch temperature regulator, an overhead mechanical stirrer and $N_2$ inlet are added. To the stirred reaction is added 177.32 g of decanoyl chloride (a 1.1 molar excess) dropwise at such a rate as to maintain the temperature of the reaction at or below 50° C. The reaction is allowed to continue stirring with no heat overnight. GC analysis confirms that the reaction is complete.

35 g of methanol is added to quench excess acid chloride and the sample is put on the rotavap to remove the methanol. The sample is a clear, dark orange color. It is decided to put the sample through the WFE to remove any residual acid. The WFE is set using the same conditions as the first WFE distillation. The overheads are discarded.

TABLE 6

Collection conditions for removal of methyl decanoate.

| Jacket (° C.) | Cold Finger (° C.) | Stir Speed (rpm) | Pressure (mtorr) | Flow Rate (mL/min) |
|---|---|---|---|---|
| 140 | 10 | 492 | 100 | 1.5 |

100 mtorr = about 0.01 kPa 378.12 g of the sample is put into a 1000 mL, three-neck, round bottom flask. A thermometer with a thermowatch temperature regulator and an overhead mechanical stirrer are added. 42 g of magnesium silicate is added to the stirred reaction, then the reaction is heated to 70° C. for 1 h. The sample is then cooled and filtered using a 90 millimeter (mm) microfiltration apparatus with filter paper with a 1 micrometer (um) pore size. Acid number of the final product is found to be 0.05 mg KOH/1 g.

Example 5

12-HMS/2-Ethyl-1-hexanol/2-Ethylhexanoyl Chloride)

Day 1: 514 g of 2-ethyl-1-hexanol is weighed into a 2000 mL, three neck round bottom flask. A condenser, Dean Stark Trap, thermometer with a thermowatch temperature regulator, an overhead mechanical stirrer, stopper, and $N_2$ inlet are added. The stirrer is turned on. An amount of 1 cube of Na metal (flattened, cut into small pieces) is added to the flask. The heat is turned up to 60° C. The Na dissolves after 45 minutes. 300 g of 12-HMS is added to the flask. Insulation is wrapped around the flask. The heat is turned up to 160° C. The reaction mixes for 6 h and is allowed to continue overnight. This continues through Day 2 and Day 3.

On Day 4, after 4 h, GC confirms that the reaction is complete. 12 mL of Methanol is collected. When the reaction is cooled, 100 mL of deionized (DI) water ($H_2O$) is added and neutralized with 150 mL 1N HCl. Three water washes are done and separated using a separatory funnel. The aqueous layer is discarded. The organic layer is put into a 2000 mL Erlenmeyer flask. $MgSO_4$, anhydrous powder, is added to the Erlenmeyer flask until the $MgSO_4$ stops clumping in the flask. The solution is still very cloudy. A column prepared with Celite is set up, toluene is added to the solution, and the solution is poured through the Celite column. The solution is then clear. To remove the toluene and excess 2-ethyl-1-hexanol, the sample is evaporated using a rotavap under vacuum. The water bath is first set at 40° C. to remove the toluene, and then the temperature is raised to 90° C. to remove the 2-ethyl-1-hexanol. 326.81 g is recovered. GC confirms that an excess of 2-ethyl-1-hexanol remains, so the sample is put through the WFE using the following conditions.

TABLE 7

Removal of excess 2-ethyl-1-hexanol.

| Jacket (° C.) | Cold Finger (° C.) | Stir Speed (rpm) | Pressure (mtorr) | Flow Rate (mL/min) |
|---|---|---|---|---|
| 150 | 10 | 484 | 100 | 2.0 |

Addition of 2-ethylhexanoyl chloride (1.2 mole excess) is carried out batchwise as described hereinafter.

Batch 1: 80.77 g of product is weighed into a 500 mL three neck round bottom flask. A condenser, thermometer with a thermowatch temperature regulator, an overhead mechanical stirrer, stopper, and $N_2$ inlet are added. The stirrer is turned on. 130 mL of toluene is added. Using an addition funnel, 36.72 g of 2-ethylhexanoyl chloride is added. After 1 h, the 2-ethylhexanoyl chloride is added and the heat is increased to 120° C. After 1 h, GC confirms that the reaction is complete. The reaction is stopped and put aside.

Batch 2: 80.04 g of product is weighed into a 500 mL, three-neck, round-bottom flask. A condenser, thermometer with a thermowatch temperature regulator, an overhead mechanical stirrer and $N_2$ inlet are added. The stirrer is turned on. 130 mL of toluene is added. Using an addition funnel, 39.9 g of 2-ethylhexanoyl chloride is added. After 1 h, the 2-ethylhexanoyl chloride is added and the heat is increased to 120° C. After 1 h, GC confirms that the reaction is complete. The reaction is stopped and put aside.

Batch 3: 132.12 g of product is weighed into a 500 mL, three-neck, round-bottom flask. A condenser, thermometer with a thermowatch temperature regulator, an overhead mechanical stirrer and $N_2$ inlet are added. The stirrer is turned on. 150 mL of toluene is added. Using an addition funnel, 69.93 g of 2-ethylhexanoyl chloride is added. After 1 h, the 2-ethylhexanoyl chloride is added. The reaction is allowed to continue stirring with no heat overnight. The next day, GC confirms the reaction is complete.

All three batches are combined in a 2000 mL, three-neck, round-bottom flask. A thermometer and an overhead mechanical stirrer are added. 300 mL of methanol is added to sample. The stirrer is started. The sample is allowed to mix for 30 minutes. The sample is put on the rotavap to remove the toluene and methanol. 431.04 g are recovered. The acid number is tested and found to be 5.39 mg KOH/g. 50.65 g of sodium hydroxide (NaOH) pellets are added to the flask and a stirrer, and the sample stirred overnight. The next day, 500 mL of hexane is added, and the sample is poured down a column that is one-quarter filled with silica 60 gel. Once the sample is pulled through, the column is rinsed with 2 aliquots of 100 mL each hexane. After the rotavap, 357.78 g is recovered. The sample is run down the WFE using the same conditions as earlier to remove any excess solvent. The overheads are discarded.

What is claimed is:

1. A process for preparing a dielectric fluid composition comprising (a) reacting 12-hydroxy methyl stearate and a linear or branched C3 to C20 alcohol under conditions suitable to form an alkyl-12-hydroxy stearate; and (b) reacting the alkyl-12-hydroxy stearate and a carboxylic acid selected from the group consisting of linear and branched C4-C20 free acid chlorides, fatty acids, carboxylic acid anhydrides, and combinations thereof, under conditions suitable to form a functionalized 12-hydroxy stearic acid.

2. The process of claim 1, wherein the alcohol is selected from the group consisting of C8 to C10 alcohols.

3. The process of claim 1, wherein the carboxylic acid is selected from linear and branched C8 to C10 fatty acids and carboxylic acid anhydrides.

4. The process of claim 1, wherein the carboxylic acid is a linear or branched C8 to C10 free acid chloride.

* * * * *